(12) United States Patent
Kato

(10) Patent No.: US 11,857,971 B2
(45) Date of Patent: Jan. 2, 2024

(54) TEST DEVICE AND TEST METHOD

(71) Applicant: ICST CORPORATION, Saitama (JP)

(72) Inventor: Yasunori Kato, Saitama (JP)

(73) Assignee: ICST CORPORATION

( * ) Notice: Subject to any disclaimer, the term of this patent is extended or adjusted under 35 U.S.C. 154(b) by 679 days.

(21) Appl. No.: 16/955,446

(22) PCT Filed: Dec. 21, 2018

(86) PCT No.: PCT/JP2018/047153
§ 371 (c)(1),
(2) Date: Jun. 18, 2020

(87) PCT Pub. No.: WO2019/131475
PCT Pub. Date: Jul. 4, 2019

(65) Prior Publication Data
US 2020/0346217 A1 Nov. 5, 2020

(30) Foreign Application Priority Data
Dec. 28, 2017 (JP) .................. 2017-253140

(51) Int. Cl.
*B01L 3/00* (2006.01)
*C12M 1/30* (2006.01)

(52) U.S. Cl.
CPC ............. *B01L 3/565* (2013.01); *C12M 33/02* (2013.01); *B01L 2200/0689* (2013.01)

(58) Field of Classification Search
CPC .. B01L 3/565; B01L 2200/0689; C12M 33/02
See application file for complete search history.

(56) References Cited

U.S. PATENT DOCUMENTS

| 5,403,551 A | 4/1995 | Galloway et al. |
| 5,620,657 A | 4/1997 | Sizto et al. |
| 5,622,870 A | 4/1997 | Sizto et al. |

(Continued)

FOREIGN PATENT DOCUMENTS

| CN | 104062430 A | 9/2014 |
| JP | H08-503556 A | 4/1996 |

(Continued)

OTHER PUBLICATIONS

Office Action issued in the corresponding Chinese Application No. 201880084732X; dated Feb. 13, 2023 (total 20 pages).

*Primary Examiner* — Jennifer Wecker
*Assistant Examiner* — Kathryn Elizabeth Limbaugh
(74) *Attorney, Agent, or Firm* — Harness, Dickey & Pierce, P.L.C.

(57) ABSTRACT

A test device and a test method are provided which can prevent a specimen liquid from splattering and leaking and perform an examination simply and safely. The test device includes a culturing unit configured to be capable of culturing a specimen in a sealed state, a test piece configured to be capable of absorbing a specimen liquid in the culturing unit, a separating unit configured to be capable of separating the test piece and the specimen liquid in a non-contact state, an opening unit configured to be capable of opening at least a portion of the separating unit to form a flow path through which the specimen liquid reaches the test piece, and a case configured to integrally seal at least a portion of the test piece on a side closer to the separating unit, at least a portion of the culturing unit, and the separating unit.

16 Claims, 6 Drawing Sheets

(56) References Cited

U.S. PATENT DOCUMENTS

| | | | |
|---|---|---|---|
| 6,017,494 | A | 1/2000 | Ashihara et al. |
| 6,277,646 | B1 | 8/2001 | Guirguis et al. |
| 6,555,390 | B2 | 4/2003 | Chandler |
| 10,520,497 | B2 | 12/2019 | Wada et al. |
| 2002/0004245 | A1 | 1/2002 | Chandler |
| 2007/0275475 | A1 | 11/2007 | Liang |
| 2012/0164751 | A1 | 6/2012 | Liang et al. |
| 2018/0292398 | A1 | 10/2018 | Wada et al. |

FOREIGN PATENT DOCUMENTS

| | | |
|---|---|---|
| JP | 2001-116739 A | 4/2001 |
| JP | 2001-513897 A | 9/2001 |
| JP | 2006-029817 A | 2/2006 |
| JP | 2012-230025 A | 11/2012 |
| JP | WO2017-104143 A1 | 6/2017 |
| JP | 6217141 B2 | 10/2017 |
| WO | 98-38917 A1 | 9/1998 |

TEST DEVICE AND TEST METHOD

CROSS REFERENCE TO RELATED APPLICATIONS

This application is a U.S. National Phase Application of International Application No. PCT/JP2018/047153, filed on Dec. 21, 2018, which claims priority to Japanese Application No. 2017-253140, filed on Dec. 28, 2017. The entire disclosures of the above applications are incorporated herein by reference.

BACKGROUND

Technical Field

The present invention relates to a test device and a test method for performing a biomolecule detection test with test piece paper.

Related Art

There is known a test device in which a test piece, to which a reagent and an indicator and the like are attached, is allowed to absorb a liquid to be determined, and the test piece in a state in which the reagent and the like and the liquid to be determined have reacted with each other is viewed for determination.

A known example of the above-described test device is a test device used in, for example, an immunological examination by a method (for example, immunochromatography) of detecting biomolecules such as antigens in living bodies. Such a test device employs a property (capillary action) in which a specimen slowly flows in a porous test piece while dissolving a reagent therein.

Immunochromatography is an immunological examination method based on an antigen-antibody reaction as principle. In this method, a porous test piece containing previously immobilized labeled antibodies and capture antibodies is prepared, and a specimen liquid is absorbed into one end of the test piece. Biomolecules (antigens or the like) in the specimen liquid migrate on the test piece by capillary action while forming immune complexes with labeled antibodies. Since the immune complexes are colored when captured by the capture antibodies to become a state in which colored particles derived from the labeled antibodies are concentrated, the colored state is viewed as the degree of the antigens contained in the specimen for determination.

According to this method, a simple and quick examination is enabled by a simple test device. This method is currently widely adopted for the detection of the influenza virus, O157, and the like, and a pregnancy test, and the like.

A known example of the test device by immunochromatography is a test device in which a test piece containing previously immobilized labeled antibodies and capture antibodies is enclosed in a rectangular case having a dropping window of a specimen liquid and a detection window through which the state of the test piece is viewed (for example, see Japanese Patent No. 6217141).

However, the test device disclosed in Japanese Patent No. 6217141, for example, had a problem in that safety is not sufficient depending on an object to be examined.

For example, in detecting bacteria such as O157 as biomolecules, bacteria are sampled from an environment where adhering bacteria exist, and the sampled bacteria are cultured to a considerable number (for example, cultured to 1000 times). Then, the specimen liquid after culture needs to be dropped into the test device for testing.

In this case, with the test device like those disclosed in Japanese Patent No. 6217141, the operator needs to manipulate a dropper, in which the specimen liquid containing a high concentration of bacteria is housed, for dropping the specimen liquid on the test piece from the dropping window of the test device. Thus, a careful attention needs to be paid such that the operator does not touch the specimen liquid.

Therefore, the examination needed to be performed by a skilled operator in a specialized institution. Furthermore, even if so, there is still a risk that the specimen liquid may splatter or leak to the surroundings or may be brought into contact with the operator, which causes secondary contamination or infection.

In view of the above-described circumstances, an object of the present invention is to provide a test device and a test method which can prevent a specimen liquid from splattering and leaking and perform an examination simply and safely.

SUMMARY

The present invention is a test device including a culturing unit configured to be capable of culturing a specimen in a sealed state, a test piece configured to be capable of absorbing a specimen liquid in the culturing unit, a separating unit configured to be capable of separating the test piece and the specimen liquid in a non-contact state, an opening unit configured to be capable of opening at least a portion of the separating unit to form a flow path through which the specimen liquid reaches the test piece, and a case configured to integrally seal at least a portion of the test piece on a side closer to the separating unit, at least a portion of the culturing unit, and the separating unit.

Also, the present invention is a test method for detecting a biomolecule using a test device in which a culturing unit of a specimen and a test piece are retained by an integral-type case. The test method includes a step of sampling the specimen in a state in which the culturing unit and the test piece are separated and culturing the specimen in the culturing unit in a sealed state, a step of releasing the separation between the culturing unit and the test piece while the sealed state by the case is maintained such that the test piece is caused to absorb a specimen liquid after culture without being exposed to outside, and a step of viewing the test piece for determination.

Advantageous Effects of Invention

According to the present invention, a test device and a test method which can prevent a specimen liquid from splattering and leaking to perform an examination simply and safely can be provided.

BRIEF DESCRIPTION OF THE DRAWINGS

FIG. 2A is a side cross-sectional view of the test device, FIG. 2B is a view illustrating a state of sampling by a sampling unit, and FIG. 2C is a side cross-sectional view illustrating a state during culture.

FIG. 3A is a side cross-sectional view of the test device, FIG. 3B is a partial enlarged view of a side cross section of the test device, FIG. 3C is a partial enlarged view of a side cross section of the test device, and FIG. 3D is a top view of the test device.

DETAILED DESCRIPTION

Figure 1A:
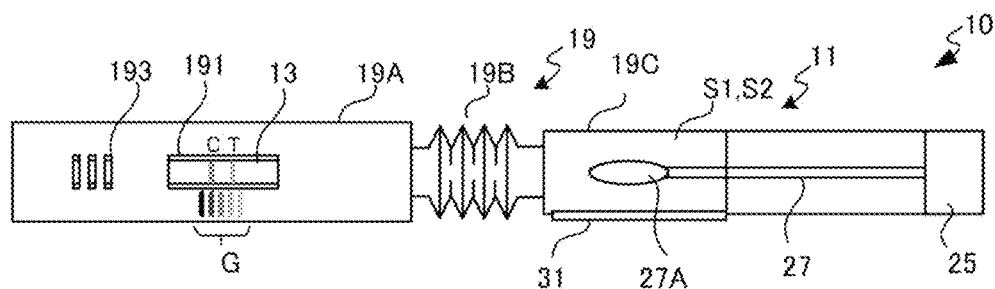
FIG. 1A is a top view of a test device according to an embodiment of the present invention.

Hereinafter, an embodiment of the present invention will be described with reference to the drawings.
Test Device FIG. 1A to FIG. 6D are views illustrating examples of the embodiment of the present invention. Portions assigned with the same reference numeral in the drawings indicate the same member. It is noted that in the drawings, some of the structures are appropriately omitted for the simplification of the drawings. The size, shape, thickness, and the like of the members are appropriately exaggerated.

Figure 1B:
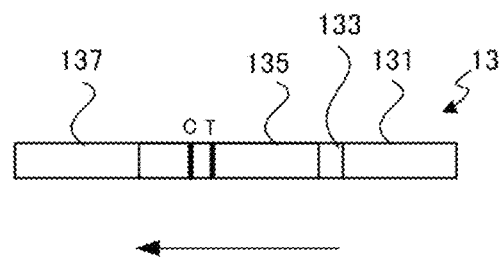
FIG. 1B is a top view of a test piece.
Figure 1C:
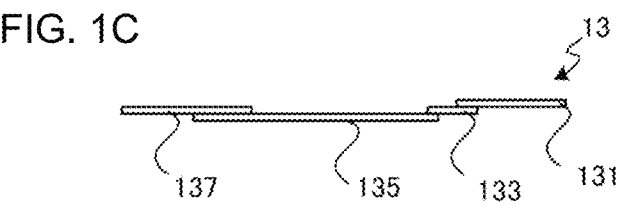
FIG. 1C is a side view of the test piece.
Figure 1D:
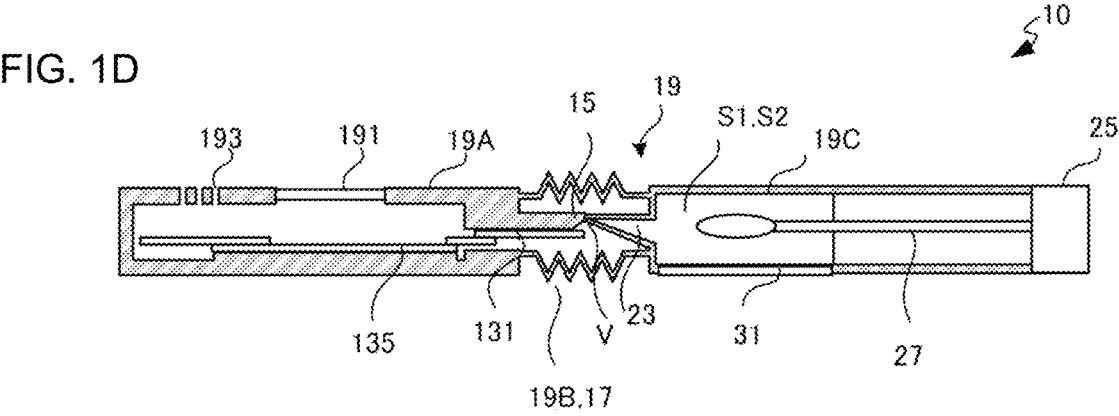
FIG. 1D is a side cross-sectional view of the test device.

FIGS. 1A-1D includes views illustrating a test device 10 according to the present embodiment. FIG. 1A is a top view illustrating its appearance, FIG. 1B is a top view illustrating an example of a test piece 13, FIG. 1C is a side view of the test piece 13, and FIG. 1D is a side cross-sectional view illustrating a state before testing (before a specimen liquid S2 drops on the test piece 13) as well as an unused state of the test device 10.

As illustrated in FIGS. 1A-1D, the test device 10 of the present embodiment includes a culturing unit 11, a test piece 13, a separating unit 15, an opening unit 17, and a case 19.

As illustrated in FIG. 1D, the culturing unit 11 includes, for example, a solution housing part 19C, a flow path 23 of a specimen liquid S2, and a sealing unit (for example, a screw cap) 25 to seal the solution housing part 19C.

In the solution housing part 19C, a culture solution S1 is housed before testing. The culture solution S1 can culture a specimen to a considerable number (for example, 1000 times). Also, the solution housing part 19C can subsequently house a solution (hereinafter, referred to as a "specimen liquid S2") containing a considerable number of specimens after cultured.

More specifically, the solution housing part 19C can house a sampling unit 27 (in this example, a cotton swab or the like) with a sampled specimen as it is. The sampling unit 27 is, for example, a rod-like member (in this example, a cotton swab or the like) having a sampling part 27A on one end thereof. According to the culturing unit 11, the sampling unit 27 is housed in the solution housing part 19C such that the sampling part 27A (the tip of the cotton swab) is immersed in the culture solution S1. Furthermore, the sampling unit 27 is sealed by the sealing unit (cap) 25 so as to be housed in a sealed state, so that the specimen can be cultured.

A metal plate 31 having high thermal conductivity or the like may be disposed on a portion of the outer surface of the solution housing part 19C. The metal plate 31 facilitates the transmission of exterior heat to the inside of the solution housing part 19C during culture. Accordingly, the responsivity of the culture temperature control improves, so that the culture can be easily facilitated.

It is noted that in this example, the cap 25 is mounted to the rear end portion (an end portion opposite to the sampling part 27A) of the sampling unit 27. Thus, the test device is configured such that when the sampling unit 27 with a sampled specimen is housed in the solution housing part 19C and the cap 25 is fitted to the rear end portion of the solution housing part 19C, the sampling part 27A is immersed in the culture solution S1.

The test piece 13 is, for example, a band-like porous member that can absorb the specimen liquid S2 cultured by the culturing unit 11. In this example, the test piece 13 is a known test piece used in an immunochromatographic assay.

More specifically, for example, as illustrated in FIG. 1B and FIG. 1C, the test piece 13 is a member that includes a sample pad 131 to serve as a dropped portion of the specimen liquid S2, a conjugate pad 133 containing antibodies (labeled antibodies) labeled with colored particles such as gold nanoparticles, a membrane filter 135 containing capture antibodies (T) and control antibodies (C), for example, linearly applied and immobilized in the width direction of the band, and an absorption pad 137 to absorb the dropped specimen liquid S2. These constituents are laminated such that their end portions superimpose each other in the band lengthwise direction. The specimen liquid S2 dropped on the sample pad 131 migrates in the arrow direction toward the absorption pad 137.

It is noted that the test piece 13 is not limited to a laminated structure in which the sample pad 131, the conjugate pad 133, the membrane filter 135, and the absorption pad 137 each partly superimpose each other as illustrated in FIG. 1C. For example, the test piece 13 may have a structure of a single band-like porous member in which the sample pad 131, the conjugate pad 133, the membrane filter 135, and the absorption pad 137 are continuously disposed along the band lengthwise direction such that their respective corresponding regions are next to each other or a structure in which some of these constituents are laminated.

In the following description, the test piece 13 having a laminated structure as illustrated in FIG. 1C will be described as an example. However, when the test piece 13 has a shape of a single band (or a band in which some of the constituents superimpose each other), the constituents described as the sample pad 131, the conjugate pad 133, the membrane filter 135, and the absorption pad 137 should be read as regions corresponding to the respective constituents. For example, when "the sample pad 131" is described, it should be read as "a region corresponding to the sample pad 131".

In this example, the case 19 includes a test piece housing part 19A, a linking unit 19B, and the solution housing part 19C. In brief, the solution housing part 19C of the culturing unit 11 is disposed integrally with the test piece housing part 19A without any space therebetween.

The test piece housing part 19A has a shape of, for example, a substantially rectangular parallelepiped inside which the test piece 13 is housed. Also, a determination window 191 through which a determination region (that is, the membrane filter 135) of the test piece 13 can be determined (viewed) from the outside and an evaporation window 193 that prevents the specimen liquid S2 from flowing back in the test piece 13 are provided to a surface (the upper surface in FIG. 1D) facing to the test piece 13 of the test piece housing part 19A.

The determination window 191 is covered with a transparent resin, glass, or the like. The evaporation window 193 opens and communicates with (opens to) the inside, but is sufficiently small to such a degree that allows the evaporation of the vaporized specimen liquid S2. With this configuration, the test piece 13 in the inside cannot be touched through these windows.

It is noted that a guide G for visual determination may be provided to a portion of the determination window 191 by, for example, affixing a sticker or printing. As the guide G, a scale of a plurality of settings (for example, 10 settings) which represents color shading levels is indicated so that the guide G serves as an index of the colored state of (the control antibodies of) the membrane filter 135. Alternatively, only one color as a criterion may be indicated instead of the color shading levels.

The linking unit 19B is a site where it is in intimate contact with both the test piece housing part 19A and the solution housing part 19C without any space and integrally links the test piece housing part 19A and the solution housing part 19C. Also, the linking unit 19B is configured to be, for example, bendable and deformable. Here, as an example, the linking unit 19B has a bellows structure such that the test piece housing part 19A and the solution housing part 19C are linked and retained in a relatively foldable manner.

In the test device 10 of the present embodiment, the culturing unit 11 and the test piece 13 are aligned along the lengthwise direction of the case 19. The culture solution S1 or the specimen liquid S2 in the culturing unit 11 after culture and the test piece 13 are sealed and retained integrally by the case 19 (the test piece housing part 19A, the linking unit 19B, and the solution housing part 19C). However, before testing by the test device 10 (before the specimen liquid S2 drops on the test piece 13), the culture solution S1 or the specimen liquid S2 and the test piece 13 are separated by the separating unit 15 in a non-contact state as illustrated in FIG. 1D.

The separating unit 15 is, for example, a sealing member that is housed inside the linking unit 19B of the case 19 and prevents the specimen liquid S2 from being brought into contact with the test piece 13 until a prescribed time (a timing of testing). In this example, the separating unit 15 is provided as a portion of the case 19 (integrally with the case 19).

More specifically, the flow path 23 of the specimen liquid S2 is formed in the solution housing part 19C on a side closer to the test piece 13 (a side opposite to the cap 25). In this example, the flow path 23 is, for example, smaller in diameter than the cylindrical solution housing part 19C and narrower toward a direction away from the solution housing part 19C. With this configuration, an appropriate amount of the specimen liquid S2 in the solution housing part 19C can drop on the end portion (the sample pad 131) of the test piece 13. It is noted that the shape of the flow path 23 is not limited to that illustrated in the drawing. The flow path 23 may have any shape and structure as long as the specimen liquid S2 can flow out toward the test piece 13.

In this case, the separating unit 15 is in contact with the outflow-side end portion (opening) of the flow path 23 of the culturing unit 11 to seal the opening, above the end portion (the sample pad 131) of the test piece 13 on a side closer to the culturing unit 11. The separating unit 15 is, for example, a sealing member formed in such a manner that a portion (the inner wall of the test piece housing part 19A) of the case 19 is pulled into the inner space of the linking unit 19B.

It is noted that the contact region between the flow path 23 and the separating unit (sealing member) 15 and/or its vicinity has a fragile structure V that is more likely to be broken than other regions, such that the flow path 23 and the separating unit (sealing member) 15 can be separated by, for example, applying an (slight) external force.

Figure 3A:
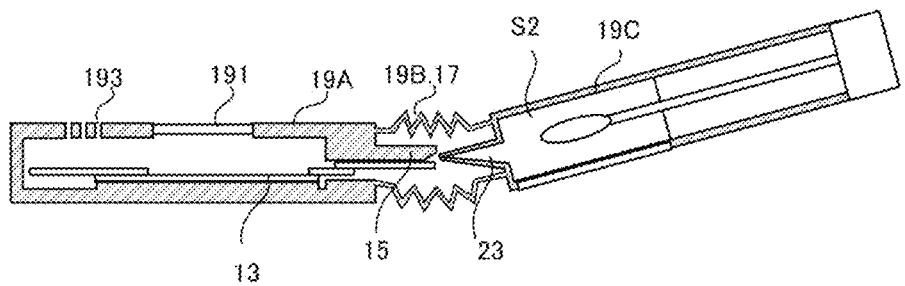
FIGS. 3A-3D include views illustrating a test method using a test device according to an embodiment of the present invention.
Figure 3B:
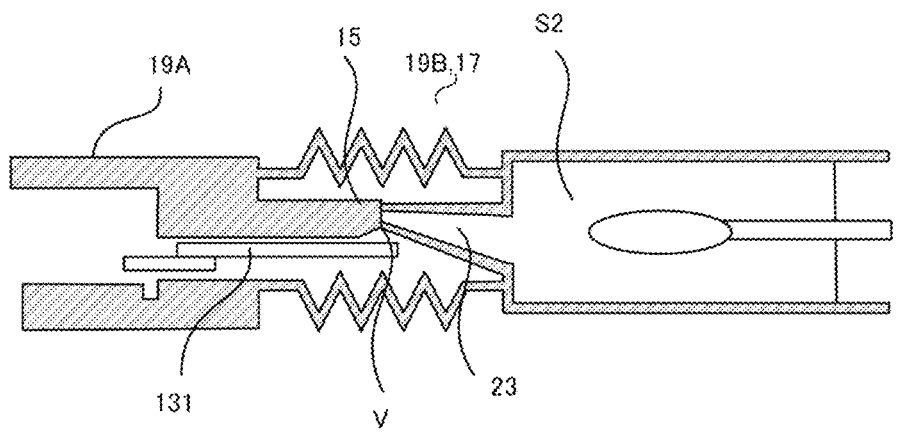

For example, in this example, at least one of the flow path 23 and the separating unit (sealing member) 15 or the contact portion therebetween, and/or its vicinity have a thin structure (see FIG. 3B). This thin structure is, for example, a structure in which the member is thinner than other sites to reduce its strength or a structure in which the member has a notch to guide the folding and separation into a prescribed direction.

For example, in FIG. 1D, the contact portion between the separating unit 15 and the flow path 23 has the fragile structure V. For example, the contact portion is folded and broken (separated) with such an external force as bending, folding, or pinching by the operator's hand and fingers. Accordingly, the separating unit (sealing member) 15 detaches from the flow path 23. Thus, the flow path 23 and the test piece housing part 19A communicate with each other, and the specimen liquid S2 drops on the sample pad 131 of the test piece 13.

In the example illustrated in FIG. 1, the opening unit 17 is the linking unit 19B which links the test piece housing part 19A and the solution housing part 19C and retains the both in a foldable manner. Specifically, for example, the operator can fold the solution housing part 19C with respect to the test piece housing part 19A (for example, fold the solution housing part 19C toward the upper side of FIG. 1D) around the opening unit 17 (linking unit 19B) of the bellows structure. Accordingly, the separating unit 15 opens from the flow path 23.

Thus, in the test device 10 of the present embodiment, the case 19 integrally seals at least a portion (the sample pad 131 portion that is a region on which the specimen liquid S2 drops) of the test piece 13 on the side closer to the separating unit 15, at least a portion (the solution housing part 19C, the flow path 23, and the tip opening of the flow path 23) of the culturing unit 11, and the separating unit (sealing member) 15. In a state before the start of testing, the culture solution S1 or the specimen liquid S2 and the test piece 13 are separated by the separating unit 15.

Furthermore, the test device 10 includes the opening unit 17 that can release the separated state (sealed state) between the specimen liquid S2 and the test piece 13 by the separating unit (sealing member) 15 to be capable of forming the flow path through which the specimen liquid S2 housed in the solution housing part 19C of the culturing unit 11 reaches the test piece 13. As already described, the opening unit 17 of this example is a portion (the linking unit 19B), which can deform in a state in which the sealing is maintained, of the case 19.

During testing, the opening unit 17 (linking unit 19B) changes its state thereby to open the separating unit 15 while the sealed state inside the case 19 is maintained.

For example, the opening unit 17 can be deformed by applying an external force in a state in which the sealing is maintained. Accordingly, the separating unit 15 opens in the state of being sealed inside the case 19. When the separating unit 15 opens, the flow path 23 and the inside of the test piece housing part 19A communicate with each other. Then, the specimen liquid S2 drops on the sample pad 131 of the test piece 13 without being exposed to the outside of the case 19.

It is noted that the separating unit 15 and/or the fragile structure V near the separating unit 15 are more likely to be broken than other regions such that the flow path 23 and the separating unit 15 can be easily separated. In the present embodiment, a structure (here, including the fragile structure V) which contributes to the opening by the opening unit 17 in this manner is also a part of the opening unit 17.

Although the opening unit 17 (linking unit 19B) has the bellows structure in this example, it may have, for example, a tube structure which is inwardly bendable or foldable with an external force or the like.

Also, at least the opening unit 17 may preferably be transparent such that the separating unit 15 and its vicinity can be viewed from the outside. Accordingly, the operator can easily check the opening state of the separating unit 15, which enables a reliable opening work.

According to such a structure, the process from the culturing of the specimen to the dropping of the specimen liquid S2 on the test piece 13 can be performed in a sealed environment. In particular, the step of dropping the specimen liquid S2, which had the risk that the specimen liquid S2 may be exposed, can be completed inside the case 19 under a substantially sealed environment. Therefore, even when the specimen liquid S2 contains a high concentration of bacteria, the specimen liquid S2 will not be exposed to the outside, and the specimen liquid S2 can be prevented from splattering and leaking. Moreover, secondary contamination and infection to the operator and the work environment can be prevented.

Furthermore, since the examination can be performed simply and safely, it can also be performed, for example, by employees of restaurants in the premises of restaurants or the like without resort to specialized institutions and skilled operators.

In the above-described example, the evaporation window 193 is provided to the case 19 for preventing the specimen liquid S2 from flowing back in the test piece 13. The evaporation window 193, however, may not be provided if the outflow can be prevented by, for example, observing a determination time or devising the shape of the test piece 13 (for example, sufficiently increasing the length in the lengthwise direction).

When the evaporation window 193 is not provided, a substantially complete sealed space can be realized in the case 19. Specifically, the test piece 13, the solution housing part 19C and the flow path 23 of the culturing unit 11, and the separating unit 15 can be sealed, which is further suitable in terms of the prevention of the splattering and leaking of the specimen liquid S2.

Detection Test Method of Biomolecules

Figure 2A:
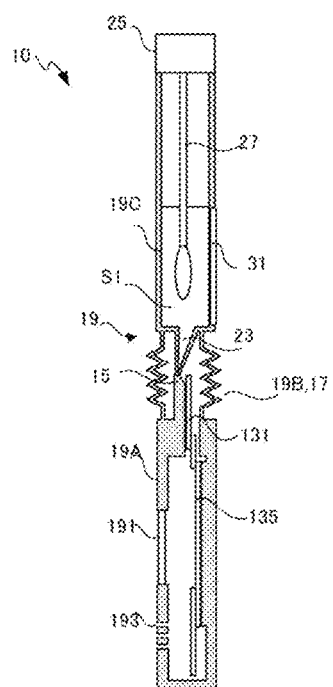
FIGS. 2A-2C include views illustrating a test method using a test device according to an embodiment of the present invention.
Figure 2B:
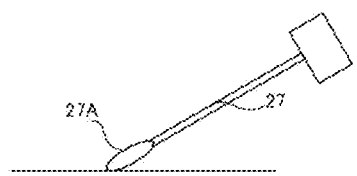

By referring to FIG. 2A to FIG. 3D, a detection test method of biomolecules using the test device 10 of the present embodiment will be described. It is noted that FIG. 3B and FIG. 3C are an enlarged view near the linking unit 19B.

First, a specimen is sampled in a sampling environment (for example, a kitchen of a restaurant) where the existence of biomolecules to be intended (detected) (for example, pathogenic *Escherichia coli* such as O157) is suspected. Specifically, an unused test device 10 of the present embodiment is prepared. As described above, the test device 10 includes the culturing unit 11 and the test piece 13 which are retained in the integral-type case 19 (FIG. 2A).

A specimen is sampled in a state in which the culturing unit 11 and the test piece 13 are separated. The sampled specimen is cultured in the culturing unit 11 in a sealed state.

Specifically, the cap 25 at the end portion of the culturing unit 11 is removed, and the sampling unit 27 is pulled out. A desired site is wiped with the sampling part 27A of the sampling unit 27 such that a specimen adheres to the sampling part 27A (FIG. 2B).

Thereafter, the sampling unit 27 is housed back in the culturing unit 11 and closed and sealed with the cap 25. The sampling part 27A (the tip of a cotton swab) is configured to be immersed in the culture solution S1 in the state of being sealed with the cap 25. Thus, the specimen can be cultured while the sampling unit 27 is housed in the sealed state.

Figure 2C:
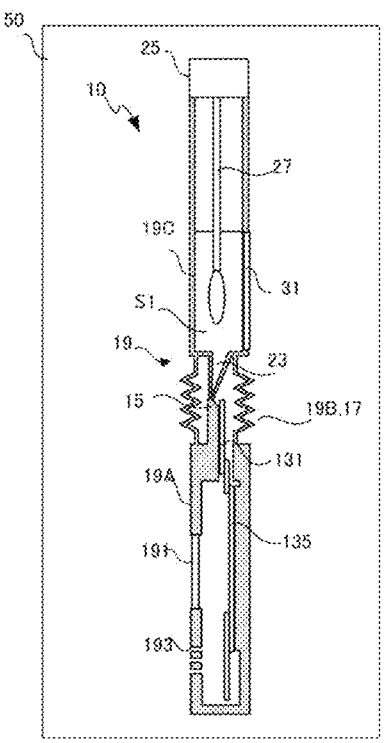
Figure 3C:
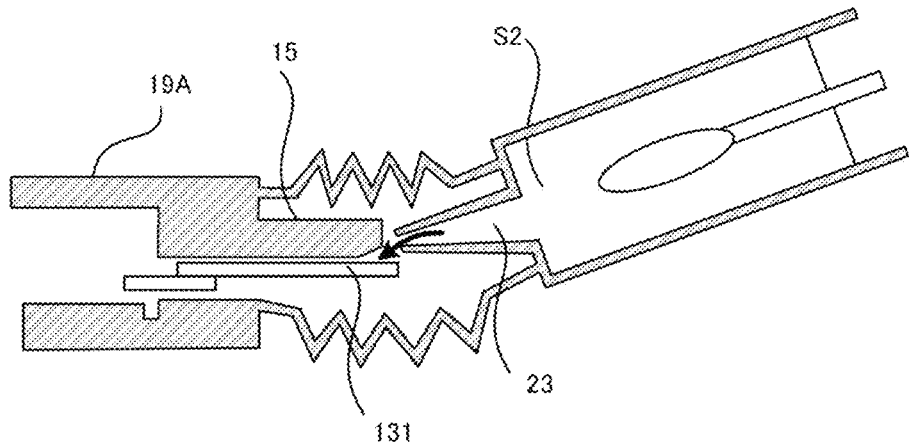

During culture, the test device 10 is stored in, for example, a constant-temperature incubator 50 and left to stand for a prescribed time (FIG. 2C). For example, when antigens are *E. coli* such as O157, the antigens are, for example, cultured at 37° C. for 3 hours to about 1000 times.

After the completion of culture, the separation between the culturing unit 11 and the test piece 13 is released while the sealed state by the case 19 is maintained. Thus, the specimen liquid S2 is absorbed by the test piece 13 without being exposed to the outside.

Specifically, the test device 10 is removed from the constant-temperature incubator 50 or the like. Then, the opening unit 17 (linking unit 19B) portion in the bellows structure is folded in the sealed state (without removing the cap 25) (FIG. 3A).

Accordingly, as illustrated in the enlarged views of FIG. 3B and FIG. 3C, the separating unit 15 is folded and broken to release the separated state inside the linking unit 19B while the sealed state by the case 19 is maintained.

Specifically, the separating unit (sealing unit) 15 detaches from the flow path 23, so that the flow path 23 and the inside of the test piece housing part 19A communicate with each other. Accordingly, while the sealed state by the case 19 is maintained, the specimen liquid S2 drops on the sample pad 131 of the test piece 13 (FIG. 3A).

The specimen liquid S2 passes through the sample pad 131 and the conjugate pad 133 and then is absorbed by the membrane filter 135 (see FIG. 1B and FIG. 1C). When antigens exist in the specimen liquid S2, the antigens migrate by capillary action in the membrane filter 135 while forming immune complexes with labeled antibodies. Since the immune complexes are colored when captured by capture antibodies to become a state in which colored particles derived from the labeled antibodies are concentrated, the coloring is viewed as the degree of the antigens contained in the specimen for determination.

Figure 3D:
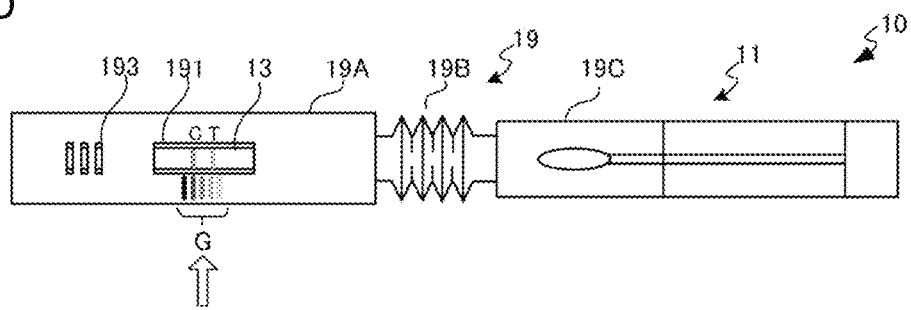

As illustrated in FIG. 3D, determination is performed by, for example, comparing the colored state of the membrane filter 135 to the guide G for visual determination disposed on a portion of the determination window 191. Alternatively, comparison may be performed using, other than the test device 10, a guide plate on which one or a plurality of color shading levels is printed.

Still alternatively, an image of the colored state of the membrane filter 135 and the guide (guide plate) taken by a mobile terminal (for example, a smartphone) may be transmitted to a determination institution for determination. Also, the taken image may be caught using a determination application program or the like for instant determination.

As described above, according to the test method using the test device 10 of the present embodiment, the process from the culturing of the specimen to the dropping of the specimen liquid S2 on the test piece 13 can be performed in a sealed environment. In particular, the step of dropping the specimen liquid S2, which had the risk that the specimen liquid S2 may be exposed, can be completed inside the case 19 under a substantially sealed environment. Therefore, even when the specimen liquid S2 contains a high concentration of bacteria, the specimen liquid S2 will not be exposed to the outside, and the specimen liquid S2 can be prevented from splattering and leaking. Moreover, secondary contamination and infection to the operator and the work environment can be prevented.

Furthermore, since the examination can be performed simply and safely, it can also be performed, for example, by employees of restaurants in the premises of restaurants or the like without resort to specialized institutions and skilled operators.

Also, when a comparison image of the colored state of the membrane filter 135 and the guide (guide plate) is transmitted to a specialized institution or captured in a specialized application program or the like for determination, unevenness in determination among operators is avoided, and accurate determination can be performed.

Modified Examples

FIG. 4A to FIG. 6D are schematic views of side cross sections mainly illustrating modified examples of the separating unit 15 and the opening unit 17 in the test device 10 of the present embodiment. It is noted that although the structures such as the test piece 13 and the test piece housing part 19A are partly omitted in FIG. 4A to FIG. 6D, the omitted structures (the test piece 13 and the test piece housing part 19A) are the same as those illustrated in FIG. 1.

Figure 4A:
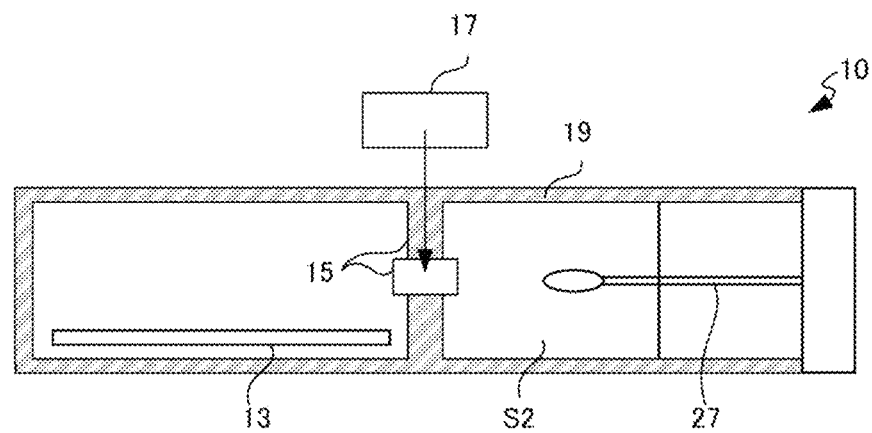
FIGS. 4A and 4B are schematic views illustrating a modified example of the test device according to the embodiment of the present invention.
Figure 4B:
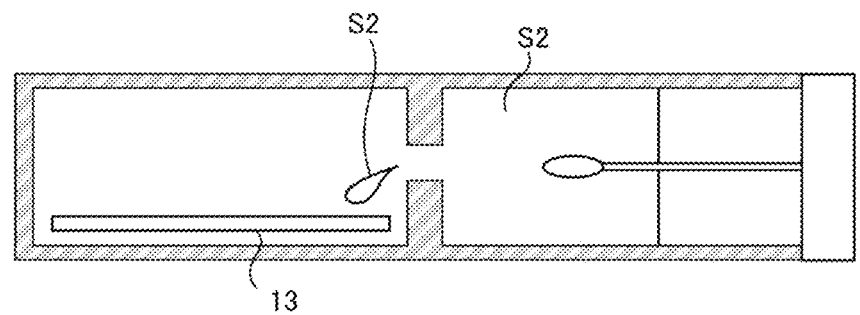

As illustrated in FIGS. 4A-4B, in the test device 10 of the present embodiment, the test piece 13 and the specimen liquid S2 are housed integrally in the case 19, and the separating unit 15 can separate at least the test piece 13 and the specimen liquid S2 in a non-contact state (FIG. 4A). During testing, (at least a portion of) the separating unit 15 opens when the operator manipulates the opening unit 17 at an optional timing. This enables the formation of a flow path through which the specimen liquid S2 reaches the test piece 13 without being exposed to the outside of the case 19 (FIG. 4B).

Figure 5A:
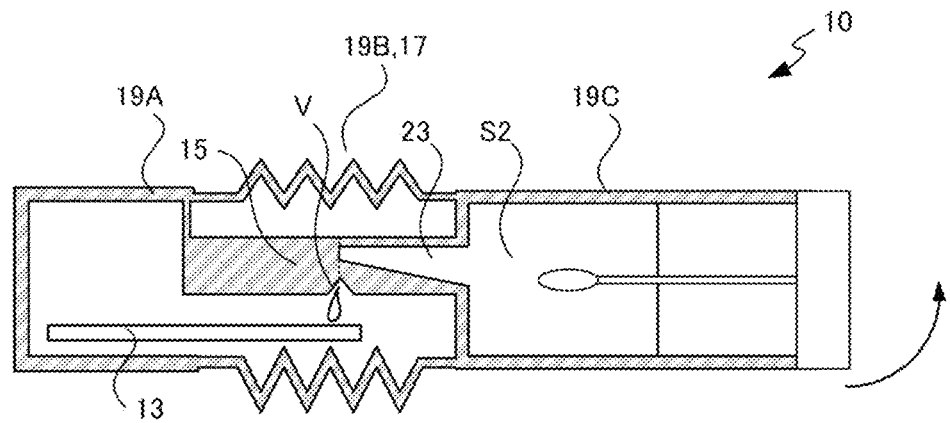
FIGS. 5A-5C are schematic views illustrating a modified example of the test device according to the embodiment of the present invention.

For example, as illustrated in FIG. 5A, the fragile structure V of the opening unit 17 may have a structure in which a notch to facilitate folding and separating in a prescribed direction (upward in FIGS. 5A-5C) is formed to one of the separating unit 15 (a portion of the test piece housing part 19A) and the flow path 23 or to their nearby member.

Figure 5B:
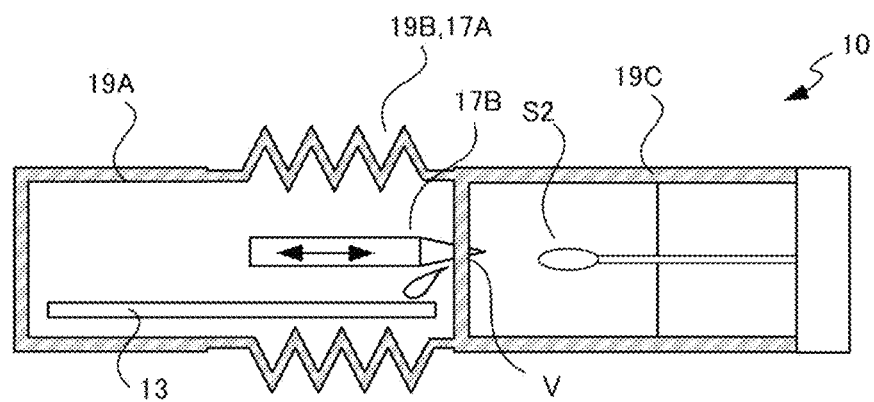

Also, as illustrated in FIG. 5B, the opening unit 17 may be, for example, the linking unit 19B (17A) stretchably disposed in the lengthwise direction of the case 19 and a needle-like member 17B protruding from the side closer to the test piece 13 to the side closer to the flow path 23 of the culturing unit 11, and the separating unit 15 may be the bottom of the solution housing part 19C.

In this case, although omitted in the drawing, the needle-like member 17B is, for example, linked integrally with the test piece housing part 19A, and the needle-like member 17B and the separating unit 15 are separated in an unused state. Then, when the linking unit 19B is shrunk after culture, the needle-like member 17B breaks (chips, or sticks to break) at least a portion of the separating unit 15.

Also, in FIG. 5B, the needle-like member 17B may be advanced solely toward the separating unit 15 by a manipulation from the outside. For example, the other end (the end portion away from the separating unit 15) of the needle-like member 17B is led to the outside of the case 19, and the operator manipulates the led end portion thereof to move the needle-like member 17B toward the separating unit 15. In this case, the linking unit 19B of the case 19 may be configured not to deform.

Also, the needle-like member 17B may be a needle-like member that advances from the side closer to the solution housing part 19C to the side closer to the test piece housing part 19A to break (chip) at least a portion of the separating unit 15.

Figure 5C:
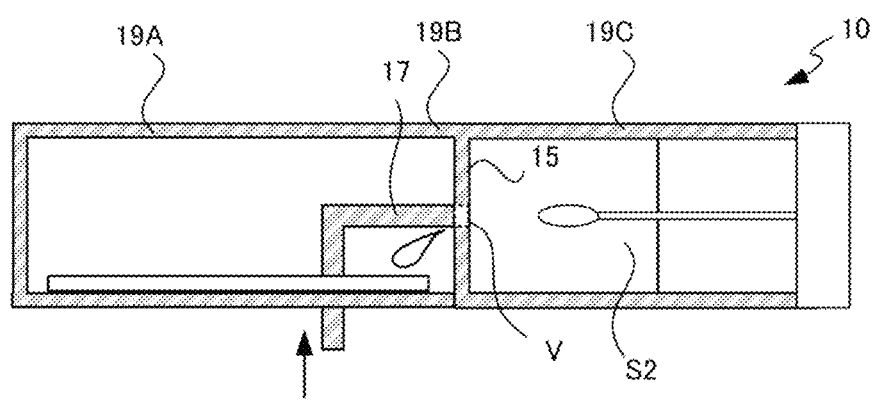

Also, as illustrated in FIG. 5C, the opening unit 17 may be formed integrally to, for example, the bottom, which serves as the separating unit 15, of the solution housing part 19C. Such an opening unit 17 may be, for example, folded and broken with respect to the separating unit 15 to chip a portion (joining part with the opening unit 17) of the separating unit 15 such that the solution housing part 19C and the test piece housing part 19A communicate with each other.

In this case, for example, the end portion opposite to the separating unit 15 of the opening unit 17 is led to the outside of the case 19, and the led portion is manipulated to fold the opening unit 17. Alternatively, although omitted in the drawing, the linking unit 19B of the case 19 may have a shape of bellows, a tube, or the like so as to be bendable and deformable as illustrated in FIG. 5A. Such a linking unit 19B may be deformed to fold the opening unit 17.

In this manner, at least a portion of the opening unit 17 of the present embodiment may be housed in the case 19 (linking unit 19B).

In both cases of FIG. 5B and FIG. 5C, the fragile structure V is provided to only a portion of the solution housing part 19C thereby to chip the separating unit 15. Thus, the opening region can be controlled (concentrated in the fragile structure V and its vicinity).

Also, in both FIG. 5B and FIG. 5C, the flow path 23 as illustrated in FIG. 5A is formed, and the separating unit 15 may be a sealing member covering the flow path 23.

Figure 6A:
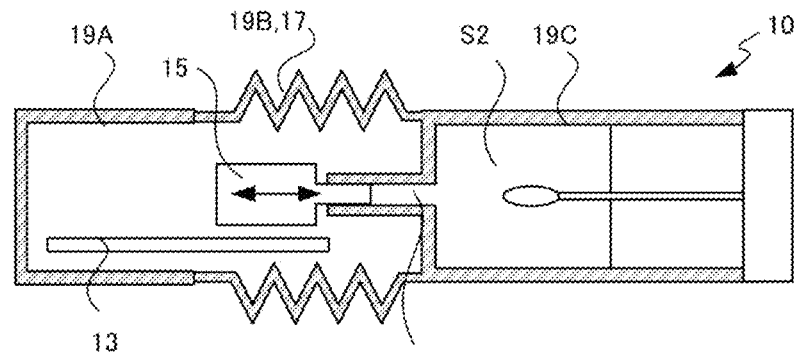
FIGS. 6A-6D are schematic views illustrating a modified example of the test device according to the embodiment of the present invention.
Figure 6B:
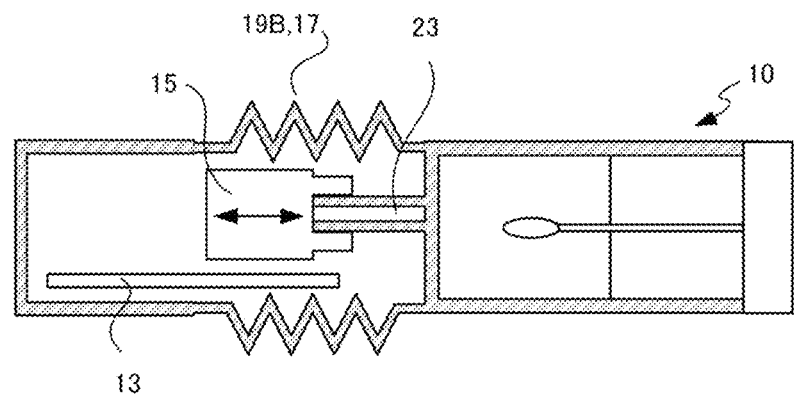

Also, as illustrated in FIG. 6A and FIG. 6B, the separating unit 15 may be a stopper member that plugs the tip of the flow path 23. In FIG. 6A, the separating unit (stopper member) 15 is inserted into the flow path 23. In FIG. 6B, the tip of the flow path 23 is inserted into the separating unit (stopper member) 15. The separating unit 15 and the flow path 23 may removably fit together by relatively moving the both in the lengthwise direction of the case 19 or may be linked together by thrusting one into the other.

In this case, although omitted in the drawing, the separating unit 15 may be linked with the test piece housing part 19A, and the separating unit (stopper member) 15 may be attachable and detachable by the manipulation of the opening unit (linking unit 19B). The opening unit 17 is, for example, the linking unit 19B, which is bendable and deformable and stretches and shrinks in the lengthwise direction of the case 19 or rotates around the rotation axis along the lengthwise direction, of the case 19. The linking unit 19B is manipulated from the outside of the case 19, so that the separating unit 15 is detached from the flow path 23.

Alternatively, a portion of the separating unit 15 may be led to the outside of the case 19, and the led portion is manipulated to attach or detach the separating unit 15.

Figure 6C:
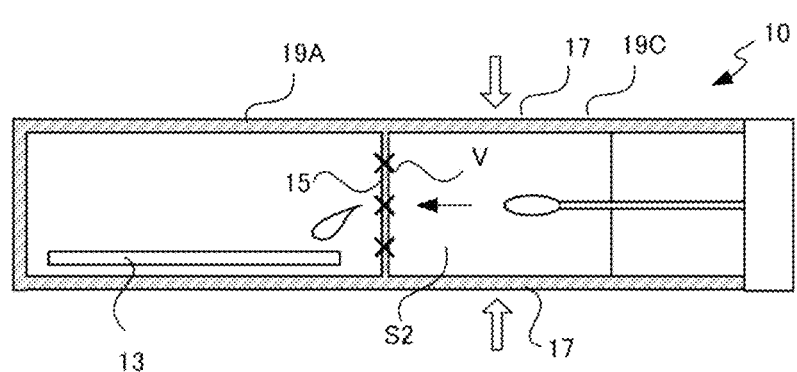

Also, as illustrated in FIG. 6C, at least a portion of the solution housing part 19C of the culturing unit 11 may be bendable and deformable. According to such a structure, when an external force is applied from the outside of the solution housing part 19C (when the solution housing part 19C is pressed), the fragile structure V provided to a portion (for example, the bottom on the side closer to the test piece 13 or the wall) of the flow path 23 or the solution housing part 19C chips (breaks). In this case, the fragile structure V and a portion of the flow path 23 or the solution housing part 19C near the fragile structure V to be chipped serve as the separating unit 15, and a bendable and deformable region of the culturing unit 11 (solution housing part 19C) capable of being pressed serves as the opening unit 17.

In the present embodiment, when the amount of the specimen liquid S2 dropping on the test piece 13 is excessively large, a stable result may not be obtained depending on the specimen and the structure of the test piece 13. The dropping amount of the specimen liquid S2 is, as an example, 100 µL to 140 µL, and preferably 250 µL to 500 µL in some cases depending on the shape of the test piece 13.

In the above-described test device 10, the shape of the flow path 23, the opened position when the solution housing part 19C is directly opened, the position and shape of the fragile structure V, the shapes of the opening unit 17 and the separating unit 15, and the aspect of opening are appropriately selected such that when an appropriate dropping amount of the specimen liquid S2 is specified, the appropriate amount can be dropped.

Figure 6D:
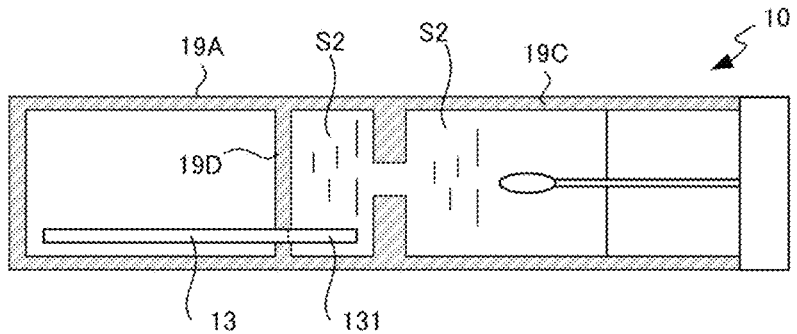

It is noted that the test device 10 of the present invention is not limited to the structure in which a portion of the specimen liquid S2 housed in the solution housing part 19C drops on the test piece 13. The test device 10 may be configured such that when the separating unit 15 is opened by the opening unit 17, a portion (for example, only the sample pad 131) of the test piece 13 is entirely immersed in the specimen liquid S2 as illustrated in FIG. 6D. In this case, a partition 19D is provided in the test piece housing part 19A. Accordingly, the test piece 13 other than the sample pad 131 is not immersed in the specimen liquid S2, and the specimen liquid S2 migrates in the test piece 13.

Also, although the determination window 191 is provided to the test piece housing part 19A in the above-described example, the determination window 191 may not be provided, and the test piece housing part 19A or the entire case may be transparent such that the inside can be viewed.

Also, although the test device 10 used in the detection test of biomolecules by immunochromatography has been described as an example in the above-mentioned embodiment, the test device 10 of the present invention may also be, without limited to immunochromatography, a test device using the test piece 13 that absorbs the specimen liquid S2 cultured by the culturing unit 11 to be capable of displaying some kind of a result or the test piece 13 that absorbs the specimen liquid S2 (in the culturing unit 11) housed in the culturing unit 11 to be capable of displaying some kind of a result.

It should be noted that the test device 10 of the present invention is not limited to the above-described embodiment and can be variously modified without departing from the scope of the present invention.

The invention claimed is:

1. A test device comprising:
a sampling unit configured to take a specimen;
a culturing unit configured to culture the specimen while the sampling unit is sealed inside the culturing unit;
a test piece configured to absorb a specimen liquid in the culturing unit;
a separating unit configured to separate the test piece from the specimen liquid so that the test piece and the specimen liquid are in a non-contact state with each other;
an opening unit housing the separating unit, the opening unit being configured to open at least a portion of the separating unit to form a flow path through which the specimen liquid reaches the test piece; and
a case including a test piece housing part that houses the test piece and a solution housing part that configures the culturing unit,
wherein the opening unit opens the portion of the separating unit by relatively displacing the test piece housing part and the solution housing part, and
a longitudinal direction of the test piece housing part is inclined with respect to a longitudinal direction of the solution housing part to open the portion of the separating unit.

2. The test device according to claim 1,
wherein at least a portion of the opening unit is housed in the case.

3. The test device according to claim 1,
wherein the test piece includes a determination region, and the case is configured such that at least the determination region can be viewed from outside.

4. The test device according to claim 1,
wherein the test piece, the culturing unit, and the separating unit are sealed in the case together.

5. The test device according to claim 4,
wherein the opening unit is a portion of the case, and while the case maintains the sealing, the opening unit is configured to be deformed by applying an external force to the opening unit to open the separating unit.

6. The test device according to claim 5, wherein
the separating unit is a sealing member configured to seal an end portion of the flow path of the culturing unit on a side closer to the test piece,
the flow path and the sealing member are housed inside the opening unit, and
the flow path and a housing region for the test piece of the case communicate with each other by detaching the sealing member from the flow path while the opening unit is deformed.

7. The test device according to claim 1,
wherein the opening unit is configured to be bendable and deformable or to be foldable and deformable.

8. A test method for detecting a biomolecule using a test device, the test device including:
a culturing unit of a specimen;
a test piece; and
an integral-type case retaining the culturing unit and the test piece, wherein the integral-type case includes a test piece housing part that houses the test piece and a solution housing part that configures the culturing unit,
the test method comprising:
a step of sampling the specimen via a sampling unit in a state in which the culturing unit and the test piece are separated by a separation unit;
a step of culturing the specimen in the culturing unit while the sampling unit and a specimen liquid are sealed inside the integral-type case;
a step of releasing the separation between the culturing unit and the test piece via an opening unit by relatively displacing the test piece housing part and the solution housing part while the sampling unit and the specimen liquid having the cultured specimen are sealed inside the integral-type case such that the test piece is caused to absorb the specimen liquid having the cultured specimen without exposing the specimen liquid having the cultured specimen to an environment outside of the integral-type case; and a step of viewing the test piece for determination, wherein a longitudinal direction of the test piece housing part is inclined with respect to a longitudinal direction of the solution housing part to release the separation between the culturing unit and the test piece.

9. The test method according to claim 8, wherein the opening unit irreversibly separates the separating unit.

10. The test method according to claim 8, wherein the separation between the culturing unit and the test piece is released by deforming the opening unit after the culturing unit is sealed with a lid.

11. The test device according to claim 1, wherein the opening unit irreversibly destroys the separating unit.

12. The test device according to claim 1, wherein the culture unit includes a lid, and the lid seals the sampling unit in the inside of the culturing unit, and a sealing operation via the lid and an opening operation via the opening unit are independent operations.

13. A test device comprising:

a sampling unit configured to take a specimen;

a culturing unit configured to culture the specimen while the sampling unit is sealed in an inside of the culturing unit;

a test piece configured to absorb a specimen liquid in the culturing unit;

a separating unit configured to separate the test piece from the specimen liquid so that the test piece and the specimen liquid are in a non-contact state with each other;

an opening unit configured to open at least a portion of the separating unit to form a flow path through which the specimen liquid reaches the test piece; and a case configured to integrally seal at least part of the test piece on a side of the separating unit, at least part of the culturing unit, and the separating unit, wherein the case includes a test piece housing part that houses the test piece, a solution housing part that configures the culturing unit, and a linking part that serves as the opening unit and links between the test piece housing part and the solution housing part, the opening unit opens the portion of the separating unit by relatively displacing the test piece housing part and the solution housing part, and a longitudinal direction of the test piece housing part is inclined with respect to a longitudinal direction of the solution housing part to open the portion of the separating unit.

14. The test device according to claim 13, wherein the test piece housing part, the linking part, and the solution housing part are arranged in this order along a longitudinal direction of the case.

15. A test method for detecting a biomolecule using a test device, the test device including:

a culturing unit of a specimen;

a test piece; and an integral-type case retaining the culturing unit and the test piece, wherein the integral-type case is configured with a test piece housing part that houses the test piece, a solution housing part that configures the culturing unit, and an opening unit that houses a separation unit, the test method comprising:

a step of sampling the specimen via a sampling unit in a state in which the culturing unit and the test piece are separated by the separation unit;

a step of culturing the specimen in the culturing unit while the sampling unit and a specimen liquid are sealed inside the integral-type case;

a step of releasing the separation between the culturing unit and the test piece via the opening unit by relatively displacing the test piece housing part and the solution housing part while the sampling unit and the specimen liquid having the cultured specimen are sealed inside the integral-type case such that the test piece is caused to absorb the specimen liquid having the cultured specimen without exposing the specimen liquid having the cultured specimen to an environment outside of the integral-type case; and a step of viewing the test piece for determination, wherein a longitudinal direction of the test piece housing part is inclined with respect to a longitudinal direction of the solution housing part to release the separation between the culturing unit and the test piece.

16. The test method according to claim 15, wherein the separating unit is housed in the integral-type case, and the separating unit is provided to be separated from the opening unit.

* * * * *